US010945780B2

(12) United States Patent
Lalonde

(10) Patent No.: US 10,945,780 B2
(45) Date of Patent: Mar. 16, 2021

(54) CRYOGENIC BALLOON DEVICE WITH ELECTROPORATION TREATMENT REGION

(71) Applicant: Medtronic CryoCath LP, Toronto (CA)

(72) Inventor: Jean-Pierre Lalonde, Candiac (CA)

(73) Assignee: Medtronic CryoCath LP, Toronto (CA)

( * ) Notice: Subject to any disclaimer, the term of this patent is extended or adjusted under 35 U.S.C. 154(b) by 579 days.

(21) Appl. No.: 15/730,063

(22) Filed: Oct. 11, 2017

(65) Prior Publication Data

US 2018/0028252 A1    Feb. 1, 2018

Related U.S. Application Data

(63) Continuation of application No. 15/347,294, filed on Nov. 9, 2016, now Pat. No. 9,808,304, which is a
(Continued)

(51) Int. Cl.
*A61B 18/02* (2006.01)
*A61B 18/14* (2006.01)
*A61B 18/00* (2006.01)

(52) U.S. Cl.
CPC .......... *A61B 18/02* (2013.01); *A61B 18/1492* (2013.01); *A61B 2018/0022* (2013.01); *A61B 2018/00255* (2013.01); *A61B 2018/00351* (2013.01); *A61B 2018/00357* (2013.01); *A61B 2018/00375* (2013.01); *A61B 2018/00613* (2013.01); *A61B 2018/00642* (2013.01); *A61B 2018/00702* (2013.01); *A61B 2018/00714* (2013.01); *A61B 2018/00791* (2013.01); *A61B 2018/00863* (2013.01); *A61B 2018/00898* (2013.01); *A61B 2018/00994* (2013.01);
(Continued)

(58) Field of Classification Search
CPC .......................... A61B 18/12; A61B 18/1492
USPC ..................................................... 606/20, 21
See application file for complete search history.

(56) References Cited

U.S. PATENT DOCUMENTS

| 5,423,807 A | 6/1995 | Milder |
| 6,787,713 B2 | 9/2004 | Kuechenmeister et al. |

(Continued)

FOREIGN PATENT DOCUMENTS

| CA | 2588367 A1 | 6/2006 |
| CN | 1703168 B | 11/2005 |

(Continued)

OTHER PUBLICATIONS

International Search Report and Written Opinion dated Feb. 6, 2013, for corresponding International Application No. PCT/CA2012/000966; International Filing Date: Oct. 19, 2012, 2012 consisting of 7 pages.
(Continued)

*Primary Examiner* — Nadia A Mahmood
(74) *Attorney, Agent, or Firm* — Christopher & Weisberg, P.A.

(57) ABSTRACT

An intravascular ablation device, including a flexible elongate body; an expandable element positioned on the elongate body; a radiofrequency or electroporation treatment segment located distally of the expandable element; a cryogenic coolant source in fluid communication with an interior of the expandable element; and a radiofrequency or electroporation energy source in communication with the radiofrequency or electroporation treatment segment.

19 Claims, 3 Drawing Sheets

Related U.S. Application Data continuation of application No. 14/932,565, filed on Nov. 4, 2015, now Pat. No. 9,510,888, which is a continuation of application No. 13/282,811, filed on Oct. 27, 2011, now Pat. No. 9,204,916.

(52) U.S. Cl.
CPC ................ *A61B 2018/0212* (2013.01); *A61B 2018/0262* (2013.01)

(56) References Cited

U.S. PATENT DOCUMENTS

| | | |
|---|---|---|
| 6,893,433 B2 | 5/2005 | Lentz |
| 7,189,227 B2 | 3/2007 | Lafontaine |
| 7,195,625 B2 | 3/2007 | Lentz |
| 9,204,916 B2 | 12/2015 | Lalonde |
| 9,510,888 B2 | 12/2016 | Lalonde |
| 2003/0187428 A1 | 10/2003 | Lane et al. |
| 2004/0220562 A1 | 11/2004 | Garabedian et al. |
| 2004/0243117 A1 | 12/2004 | Lentz |
| 2004/0243124 A1 | 12/2004 | Im et al. |
| 2008/0200828 A1 | 8/2008 | Abboud et al. |
| 2010/0069900 A1 | 3/2010 | Shirley et al. |
| 2010/0168568 A1 | 7/2010 | Sliwa |
| 2010/0274178 A1 | 10/2010 | LePivert |
| 2011/0190750 A1 | 8/2011 | Pageard |
| 2012/0136418 A1 | 5/2012 | Buckley et al. |

FOREIGN PATENT DOCUMENTS

| | | |
|---|---|---|
| CN | 101084038 B | 12/2007 |
| WO | 2008142686 A2 | 11/2008 |

OTHER PUBLICATIONS

Supplementary European Search Report dated Jul. 8, 2015, for corresponding European Application No. 12843951.0, consisting of 7 pages.

CRYOGENIC BALLOON DEVICE WITH ELECTROPORATION TREATMENT REGION

CROSS-REFERENCE TO RELATED APPLICATION

This application is a continuation of and claims priority to patent application Ser. No. 15/347,294 filed Nov. 9, 2016, which is a continuation of and claims priority to patent application Ser. No. 14/932,565, filed Nov. 4, 2015, entitled CRYOGENIC BALLOON DEVICE WITH ELECTROPORATION TREATMENT REGION, now issued as U.S. Pat. No. 9,510,888, which is a continuation of and claims priority to patent application Ser. No. 13/282,811, filed Oct. 27, 2011, entitled CRYOGENIC BALLOON DEVICE WITH RADIOFREQUENCY TIP, now issued as U.S. Pat. No. 9,204,916, the entirety of all of which is incorporated herein by reference.

STATEMENT REGARDING FEDERALLY SPONSORED RESEARCH OR DEVELOPMENT n/a

FIELD OF THE INVENTION

The present invention relates to a method and system for thermal tissue treatment, and in particular, towards systems and methods of use thereof for treating one or more tissue sites having varying geometries with varying treatment modalities.

BACKGROUND OF THE INVENTION

Minimally invasive devices, such as catheters, are often employed for surgical procedure, including those involving ablation, dilation, and the like. In a particular situation, an ablation procedure may involve creating a series of interconnecting lesions in order to electrically isolate tissue believed to be the source of an arrhythmia. During the course of such a procedure, a physician may employ several different catheters having variations in the geometry and/or dimensions of the ablative element in order to produce the desired ablation pattern. Each catheter may have a unique geometry for creating a specific lesion pattern, with the multiple catheters being sequentially removed and replaced to create the desired multiple lesions. Exchanging these various catheters during a procedure can cause inaccuracies or movement in the placement and location of the distal tip with respect to the tissue to be ablated, and may further add to the time required to perform the desired treatment. These potential inaccuracies and extended duration of the particular procedure increase the risk to the patient undergoing treatment. Accordingly, it would be desirable to provide a single medical device having the ability to provide ablative patterns of various shapes, without the need for additional catheters or the like having a single geometric orientation, and thus, limited in the ability to provide multiple ablative patterns to one or more tissue sites.

SUMMARY OF THE INVENTION

The present invention advantageously provides a medical system having multiple, independently operable treatment regions providing the ability to provide ablative patterns of various shapes. For example, a medical device is disclosed, including an elongate catheter body; a cryogenic treatment region on the catheter body; and a radiofrequency or electroporation treatment region distally of the cryogenic treatment region. The cryogenic treatment region may include an expandable element, the radiofrequency treatment region may include a substantially linear thermal segment; and the cryogenic treatment region may be operable independently from the radiofrequency treatment region. The device may include a fluid flow path in fluid communication with the cryogenic treatment region; a cryogenic fluid source in fluid communication with the first fluid flow path; a radiofrequency signal source or electrical-pulse generator coupled to the radiofrequency or electroporation treatment region; and/or a sensor coupled to at least one of the cryogenic treatment region or radiofrequency treatment region. The radiofrequency treatment region may be deflectable independently of the cryogenic treatment region.

An intravascular ablation device is disclosed, including a flexible elongate body; an expandable element positioned on the elongate body; a radiofrequency thermal segment located distally of the expandable element; a cryogenic coolant source in fluid communication with an interior of the expandable element; and a radiofrequency energy source in communication with the radiofrequency thermal segment. The radiofrequency thermal segment may include an electrically-conductive distal tip or a substantially linear, elongated electrically-conductive segment.

A method of treating cardiac tissue is disclosed, including positioning a cryogenic treatment region of a medical device proximate a pulmonary vein; ablating tissue proximate the pulmonary vein with the cryogenic treatment region; positioning a radiofrequency or electroporation treatment region of the medical device proximate the pulmonary vein; and ablating tissue proximate the pulmonary vein with the radiofrequency/electroporation treatment region. The cryogenic treatment region may include an expandable element, and positioning the expandable element may include expanding the expandable element in the pulmonary vein to substantially occlude the pulmonary vein. Ablating tissue proximate the pulmonary vein with the cryogenic treatment region may include circulating a cryogenic fluid through the expandable element. The radiofrequency or electroporation treatment region may include an electrode positioned distally of the cryogenic treatment region. Ablating tissue proximate the pulmonary vein with the cryogenic treatment region may include creating a first ablative treatment pattern, and ablating tissue proximate the pulmonary vein with the radiofrequency/electroporation treatment region may include creating a second ablative treatment pattern. The first ablative treatment pattern may include a substantially arcuate shape and/or the second ablative treatment pattern may include a substantially focal shape, and the first and second ablative treatment patterns may be substantially continuous.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
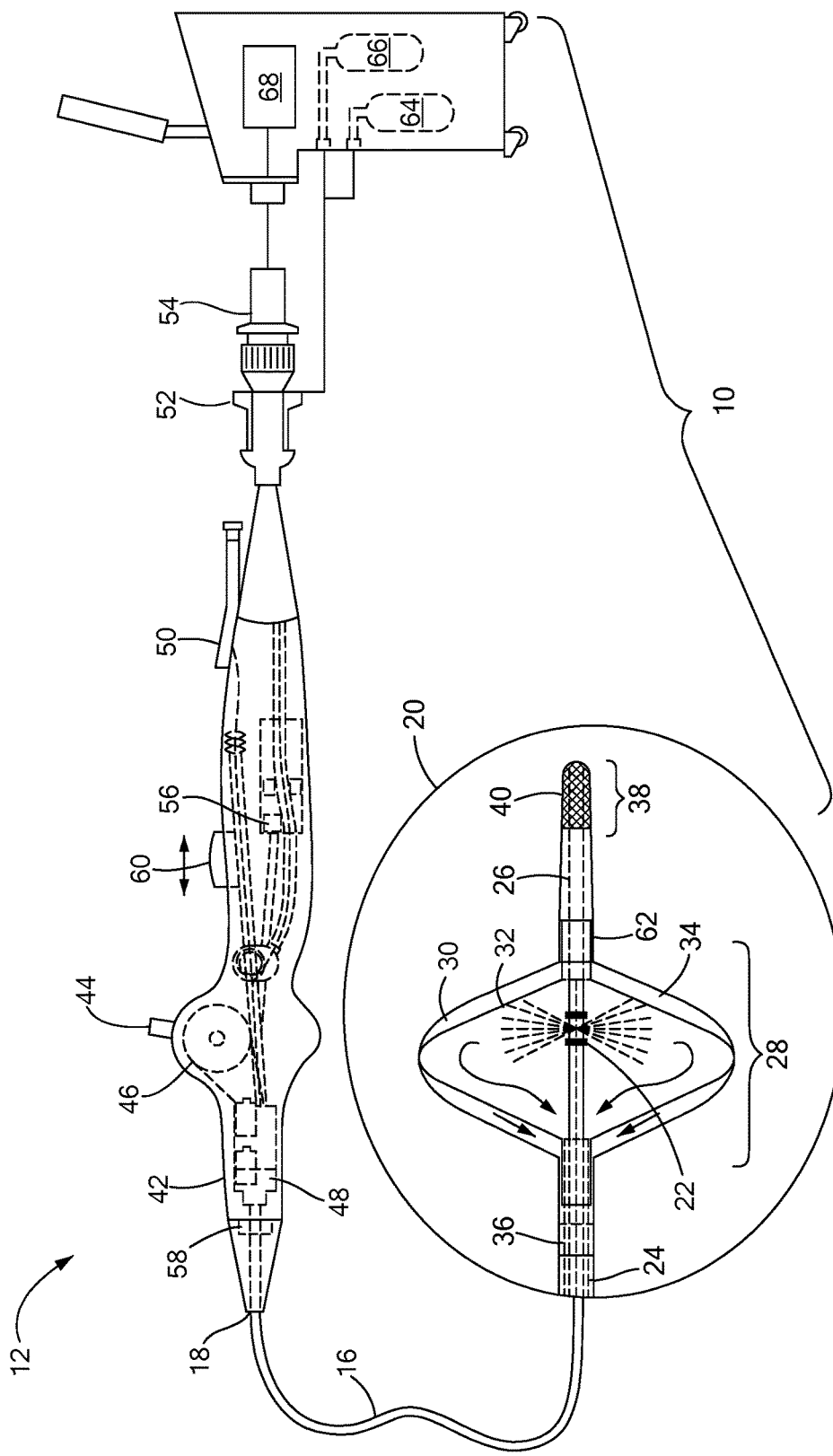
FIG. 1 is an illustration of an example of a medical system constructed in accordance with the principles of the present disclosure.

The present invention advantageously provides a medical system having the ability to provide ablative patterns of various shapes to treat one or more targeted tissue sites. Referring now to the drawing figures in which like reference designations refer to like elements, an example of a medical system constructed in accordance with principles of the present invention is shown in FIG. 1 and generally designated as "10." The system 10 generally includes a medical device 12 that may be coupled to a control unit 14. The medical device 12 may include a medical probe, a catheter, or other instrument, and may generally include one or more treatment regions for energetic or other therapeutic interaction between the medical device 12 and a treatment site. The treatment region(s) may deliver, for example, cryogenic therapy, radiofrequency energy, electroporation energy or other energetic transfer with a tissue area in proximity to the treatment region(s), including cardiac tissue.

The medical device 10 may include an elongate body 16 passable through a patient's vasculature and/or positionable proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16. For example, the elongate body 16 may include a fluid delivery or injection lumen 22 and an exhaust lumen 24 defining a fluid flow path therethrough. In addition, the elongate body 16 may include a guide wire lumen 26 movably disposed within and/or extending along at least a portion of the length of the elongate body 16 for over-the-wire applications. The guide wire lumen 26 may define a proximal end and a distal end, and the guide wire lumen 26 may be movably disposed within the elongate body 16 such that the distal end of the guide wire lumen 26 extends beyond and out of the distal portion of the elongate body 16.

The medical device 12 may include one or more treatment regions for energetic or other therapeutic interaction between the medical device 12 and a treatment site. The treatment regions may deliver, for example, radiofrequency energy, cryogenic therapy, or the like. For example, the device may include a first treatment region 28 having a thermal treatment element, such as an expandable membrane or balloon and/or one or more electrodes or other thermally-transmissive components, at least partially disposed on the elongate catheter body. In a particular example, the first treatment region 28 may include a first expandable/inflatable element or balloon 30 defining a proximal end coupled to the distal portion 20 of the elongate body 16 of the medical device 12, while further defining a distal end coupled to the distal end of the guide wire lumen 26. As such, due to the movable nature of the guide wire lumen 26 about the elongate body 16, any axial and/or longitudinal movement of the guide wire lumen 26 may act to tension or loosen the first expandable element 30, i.e., extend or retract the first expandable element 30 from a lengthened state to a shortened state during an inflation or deflation thereof. In addition, the first expandable element 30 may have any of a myriad of shapes, and may further include one or more material layers providing for puncture resistance, radiopacity, or the like. An interior chamber or region defined by the first expandable element 30 may be in communication with the fluid injection and exhaust lumens of the medical device 12 as described above, or may be fluidically isolated from either lumen.

The medical device 12 may further include a second expandable/inflatable element or balloon 32 contained within or otherwise encompassed by the first expandable element 30 such that an interstitial region, envelope or space 34 is defined therebetween. The second expandable element 32 may be in communication with the fluid injection and exhaust lumens of the medical device 12 as described above, i.e., a fluid flow path may provide an inflation fluid or coolant, such as a cryogenic fluid or the like, to the interior of the second expandable element 32. Further, the interstitial region 34 may be in fluid communication with an interstitial lumen 36 providing a fluid flow path or avenue separate and independent from a fluid flow path delivering fluid or otherwise in communication with an interior of the second expandable element 36 2. The second pathway provides an alternate exhaust route for fluid that may leak from the interior of the second expandable element into the interstitial region or fluid entering the medical device 12 from the exterior. In particular, the isolation of the interstitial lumen 36 from the interior of the second expandable element 32 provides an alternate route for fluid to circulate in the case of a rupture or leak of either the first or second expandable elements, as well as allowing for the injection or circulation of fluids within the interstitial region independently of fluids directed towards the second expandable element. Towards that end, the interstitial region 34 may be in fluid communication with a fluid source, a vacuum source, or the like separate from a fluid source, vacuum source or otherwise in fluid communication with the interior of the second expandable element. Alternatively, the interstitial lumen 36 may be joined to or otherwise in fluid communication with the exhaust lumen 24 and the interior of the second expandable element 32 to provide a single exhaust or vacuum source for the medical device 12.

Continuing to refer to FIG. 1, the medical device 12 may further include a second treatment region 38 located distally of the first treatment region 28. The second treatment region 38 is operable independently and separately from the first treatment region 28, and may provide an ablative treatment pattern different from a treatment pattern or shape provided by the first treatment region 28. In a particular example, the second treatment region 38 may provide for a "spot" or focal treatment pattern through the use of radiofrequency energy. The second treatment region 38 may include one or more electrically conductive portions or electrodes 40 coupled to a radiofrequency generator or power source. For example, the electrode(s) may be deposited or coupled to a distal portion of the elongate body 16 or guide wire lumen 26 distally of the first treatment region 28. The electrodes 40 may include variations in their number, arrangement, configuration, or shape. The electrodes 40 may be formed from metal, conductive polymers, conductive ink printing, or other electrically-conductive mediums.

The electrodes 40 may be customized to provide effective portions selected among a variety of sizes and shapes for contacting or otherwise assessing a tissue treatment area. The size, shape or length of the electrodes 40 may be limited, for example, by covering a portion of the electrode with an insulating material. The dimensions of the electrodes 40 may thus have an optimized configured having sufficient size and a geometric arrangement to effectively treat or diagnose tissue, while avoiding excessive surface area and minimizing reception of 'noise' or other signals.

The plurality of independently-controllable treatment regions provides the ability to deliver varying therapeutic treatment patterns to one or more locations. As described above, the first treatment region 28 may include one or more expandable elements or balloons. The first treatment region 28 may thus provide a first treatment pattern or shape having a substantially arcuate, circular, and/or circumferential orientation. In turn, the second treatment region 38 may include a substantially linear or focal-type electrode enabling energetic or thermal exchange with a contacted tissue area to create a second treatment pattern that includes a substantially linear or "spot" configuration. The multiple treatment patterns obtainable through the selective and independent use of the first and second treatment regions allows a user the ability to adaptively create varying treatment patterns tailored to a particular patient's anatomy and any patient-specific physiological maladies that are being diagnosed or treated with the medical device 12.

The medical system 10 may include one or more sensors to monitor the operating parameters throughout the system 10, including for example, pressure, temperature, flow rates, volume, or the like in the control unit 14, and/or the medical device 12. For example, the medical device 12 may further include one or more temperature and/or pressure sensors (not shown) proximate the treatment region(s) for monitoring, recording or otherwise conveying measurements of conditions within the medical device 12 or the ambient environment at the distal portion of the medical device 12. The sensor(s) may be in communication with the control unit 14 for initiating or triggering one or more alerts or therapeutic delivery modifications during operation of the medical device 12.

The medical device 12 may include a handle 42 coupled to the proximal portion of the elongate body 16, where the handle 42 may include an element such as a lever or knob 44 for manipulating the elongate body 16 and/or additional components of the medical device 12. For example, a pull wire 46 with a proximal end and a distal end may have its distal end anchored to the elongate body 16 at or near the distal portion 20. The proximal end of the pull wire 46 may be anchored to an element such as a cam in communication with and responsive to the lever 44.

The handle 42 can further include circuitry for identification and/or use in controlling of the medical device 12 or another component of the system 10. For example, the handle may include one or more pressure sensors 48 to monitor the fluid pressure within the medical device 12. Additionally, the handle 42 may be provided with a fitting 50 for receiving a guide wire that may be passed into the guide wire lumen 26.

The handle 42 may also include connectors that are matable directly to a fluid supply/exhaust and control unit 14 or indirectly by way of one or more intermediary coupling components. For example, the handle 42 may be provided with a first connector 52 and a second connector 54 that are matable with the control unit 14. The handle 42 may further include blood detection circuitry 56 in fluid and/or optical communication with the injection, exhaust and/or interstitial lumens. The handle 42 may also include a pressure relief valve 58 in fluid communication with the injection, exhaust and/or interstitial lumens to automatically open under a predetermined threshold value in the event that value is exceeded.

Continuing to refer to FIG. 1, the medical device 12 may include an actuator element 60 that is movably coupled to the proximal portion of the elongate body 16 and/or the handle 42. The actuator element 60 may further be coupled to the proximal portion of the guide wire lumen 26 such that manipulating the actuator element 60 in a longitudinal direction causes the guide wire lumen 26 to slide towards either of the proximal or distal portions of the elongate body 16. As a portion of either and/or both the first and second expandable elements may be coupled to the guide wire lumen 26, manipulation of the actuator element 60 may further cause the expandable element(s) to be tensioned or loosened, depending on the direction of movement of the actuator element 60, and thus, the guide wire lumen 26. Accordingly, the actuator element 60 may be used to provide tension on the expandable element(s) during a particular duration of use of the medical device 12, such as during a deflation sequence, for example. The actuator element 60 may include a thumb-slide, a push-button, a rotating lever, or other mechanical structure for providing a movable coupling to the elongate body 16, the handle 42, and/or the guide wire lumen 26. Moreover, the actuator element 60 may be movably coupled to the handle 42 such that the actuator element is movable into individual, distinct positions, and is able to be releasably secured in any one of the distinct positions.

The second treatment region 38 may be deflectable, steerable, or otherwise manipulated into a desired position or configuration independently or differently from the first treatment region 28 and/or adjacent portions of the elongate body 16. In particular, the elongate body 16 of the medical device 12 may be constructed from one or more layers of material or differing components to provide a desired degree of flexibility while maintaining the capability to transmit torque along the length of the medical device 12. The layers may include a multitude of polymers, plastics, and composites thereof, as well as braided or other structural reinforcing materials/components running therethrough. The elongate body 16 may further include one or more steering wires or actuation mechanisms to deliver a force to a particular segment or portion of the medical device 12, such as a region proximate to the second treatment region 38, in addition to the pull wire described above, which may provide deflection or steering of the first treatment region 28. The medical device 12 may also include a deformational or deflectable segment 62 between the first and second treatment regions that aids in the manipulation of the second treatment region 38 with respect to the first treatment region 28. For example, the deflectable segment may include a bellows-like region, varying material thickness or bending characteristics, or other features providing ease of deflection or movement of the second treatment region 38 with respect to the first treatment region 28.

In an exemplary system 10, a fluid supply 64 including a coolant, cryogenic refrigerant, or the like, an exhaust or scavenging system (not shown) for recovering or venting expended fluid for re-use or disposal, as well as various control mechanisms for the medical system 10 may be housed in the control unit 14. In addition to providing an exhaust function for the fluid supply, the control unit 14 may also include pumps, valves, controllers or the like to recover and/or re-circulate fluid delivered to the handle, the elongate body 16, and treatment region(s) of the medical device 12. A vacuum pump 66 in the control unit 14 may create a low-pressure environment in one or more conduits within the medical device 12 so that fluid is drawn into the conduit(s) of the elongate body 16, away from the treatment region(s), and towards the proximal end of the elongate body 16. The control unit may also include a radiofrequency signal generator or power source 68 in electrical communication with the electrodes 40. The control unit 14 may include one or more controllers, processors, and/or software modules containing instructions or algorithms to provide for the automated operation and performance of the features, sequences, or procedures described herein.

The power source 68 may optionally provide electrical pulses to the medical device 12 to perform an electroporation procedure, as described in U.S. patent application Ser. No. 13/194,259, filed Jul. 29, 2011, the entirety of which is hereby incorporated by reference. "Electroporation" utilizes high electric field amplitude electrical pulses to effectuate a physiological modification (i.e., permeabilization) of the cells to which the energy is applied. Such pulses may be short (e.g., nanosecond, microsecond, or millisecond pulse width) in order to allow application of high voltage without large flow of electrical current that would result in significant tissue heating. In particular, the pulsed energy induces the formation of microscopic pores or openings in the cell membrane. Depending upon the characteristics of the electrical pulses, an electroporated cell can survive electroporation (i.e., "reversible electroporation") or die (i.e., irreversible electroporation, "IEP"). Reversible electroporation may be used to transfer agents, including large molecules, into targeted cells for various purposes.

Figure 2:
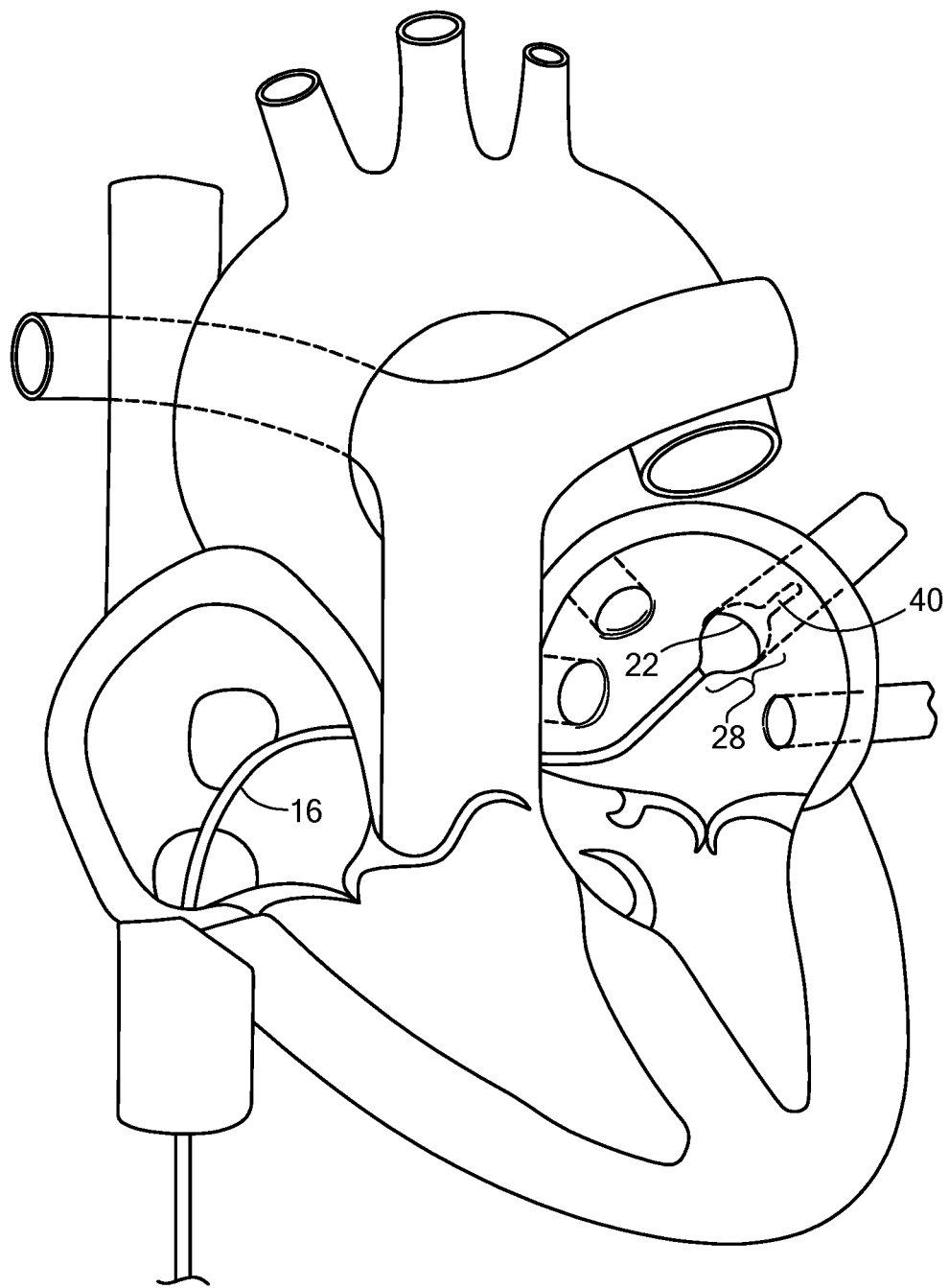
FIG. 2 is an illustration of an exemplary use of the medical system of FIG. 1.
Figure 3:
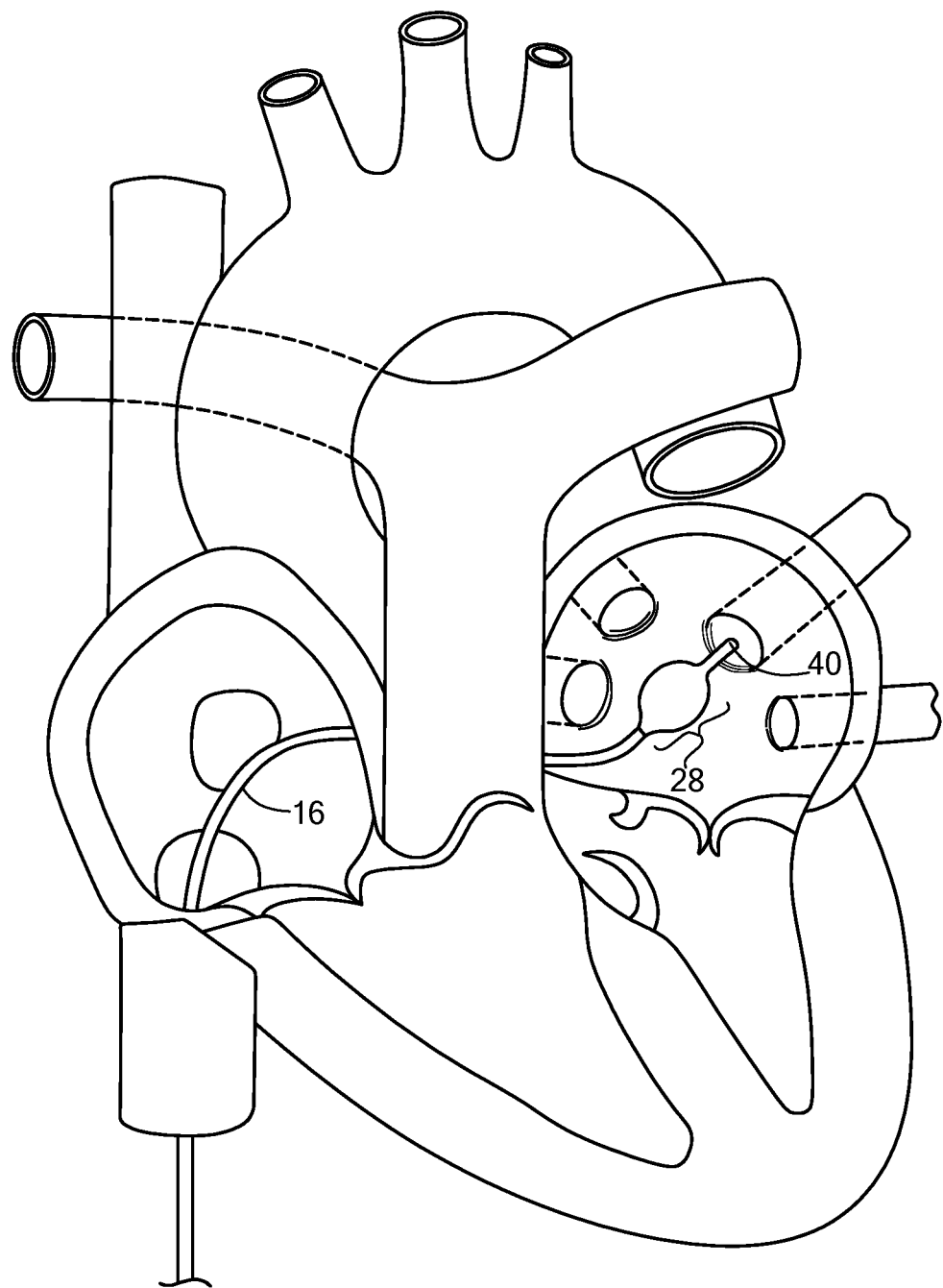
FIG. 3 is an additional illustration of an exemplary use of the medical system of FIG. 1.

Now referring to FIGS. 2-3, in an exemplary method of use, the medical system 10 may be used to deliver multiple therapeutic treatment patterns to one or more targeted tissue areas 70. For example, the medical device 12 may be positioned and operated to ablate targeted tissue region(s) in the heart. The first treatment region 28 may be positioned in the proximity of a pulmonary vein opening or junction with a portion of the atrial wall. Such positioning may be aided or facilitated by visualization methods including fluoroscopy or the like as known in the art. Where the first treatment region 28 includes an expandable element, the expandable element may be inflated or otherwise expanded to substantially occlude the pulmonary vein. The occlusion reduces the blood flow around the treatment region, thereby allowing enhanced thermal exchange between the medical device 12 and the targeted tissue.

Once the first treatment region 28 has been positioned where desired, it may be operated to affect a desired therapy, such as tissue ablation. For example, the tissue ablation may be achieved by the circulation of a cryogenic fluid from the source and/or control unit 14, to the elongate body 16, and through the expandable elements of the first treatment region 28. The first treatment region 28 may be used to create a first treatment pattern on the targeted tissue, and may include a substantially arcuate or rounded orientation around at least a portion of the pulmonary vein. Circulation of the coolant through the first treatment region 28 may continue until a desired amount of tissue, e.g. a volume or depth of the tissue, has been ablated or otherwise treated. The extent of the tissue freezing with the medical device 12 may be assessed or ascertained by measuring impedance on or about the medical device 12 and the tissue region (using the electrodes 40 for example), by implementing visualization or imaging modalities distinguishing between frozen and non-frozen tissue masses, or by providing coolant circulation under predetermined parameters (such as pressure, flow rate, delivery duration, etc.) that have previously been established as providing the desired effect under experimental or preclinical investigation.

Upon achieving the desired tissue freezing depth or extent, circulation through the first treatment region 28 may cease, the first treatment region 28 may be thawed either actively or passively by the surrounding blood flow, and the medical device 12 may be repositioned or otherwise manipulated to direct the second treatment region 38 proximate to the pulmonary vein or other tissue region (FIG. 3). Such positioning may again be aided or facilitated by visualization methods including fluoroscopy or the like as known in the art. In addition, coolant may be directed into the first treatment region 28 to create a sufficiently low enough temperature to cryoadhere the first treatment region 28 to an adjacent tissue region. Cryoadhesion may be established without allowing temperatures of the first treatment region 28 to fall low enough to cause permanent tissue injury or unwanted ablation. The first treatment region 28 may thus provide an anchoring point to stabilize the distal region of the medical device 12, thereby easing accurate placement, positioning, and/or deflection of the second treatment region 38, which may include the manipulation of one or more steering or deflection mechanisms as described herein.

The second treatment region 38 may then be used to create a second treatment pattern different from the first, either in substantial continuity with the previously-created treatment pattern or independently in another tissue region. For example, the one or more electrodes 40 of the second treatment region 38 may be powered to thermally affect or ablate the selected tissue. Powering of the electrode(s) 40 may include delivery of a radiofrequency signal or current from the radiofrequency source 68 resulting in a current flow, and thus heating, between one or more of the electrodes 40 either between each other (e.g., bipolar RF delivery) or to a ground/patient electrode (not shown) in unipolar or monopolar operation. The operation of the electrodes 40 may be controllably modulated to achieve the desired physiological affect, such as ablation. For example, the electrodes 40 may be powered by the radiofrequency signal/power source such that the electrodes 40 are maintained at a predetermined, selected temperature with the power delivered to the electrodes 40 increasing and decreasing in response to a measured temperature at or near the electrodes 40, or based upon predetermined parameters and correlations between the electrode temperature and/or electrode power delivery.

The disclosed system 10 provides a number of benefits and advantages. For example, providing multiple treatment regions with different treatment pattern capabilities allows a physician to tailor treatment to specific patients, as described above. It also allows a physician or user to create a first, larger pattern with the first treatment region 28, for example, and then follow up with the second treatment region 38 to create secondary, smaller patterns to fill in gaps or "touch up" the first treatment pattern. This may be particular convenient when attempting to isolate or otherwise ablate an anatomical structure such as a pulmonary vein (though other structures may be similarly treated) with a substantially continuous ablative pattern. The first treatment region 28 may be used to create substantially the entire desired pattern, with the second treatment region 38 used to treat missed or incongruous regions in the intended treatment region—resulting in a substantially continuous treatment pattern.

In addition, employing different treatment energy modalities (e.g., cryogenic and radiofrequency or electroporation) reduces the complexity of providing independently-controllable treatment regions that are exclusively cryogenic. For example, providing two different independently-controllable cryogenic treatment regions would include providing multiple sets of independently controllable fluid paths and associated controls (e.g., valves, regulators, or the like) in a minimally-invasive device having small dimensions and space therein, whereas a radiofrequency- or electrically-powered segment may include one or more small-dimensioned wires that are more readily integrated into the device. Furthermore, the independently controlled cryogenic treatment region may be used as a cryoadhesive anchor to facilitate secure positing and placement of the distally-located radiofrequency treatment region, as described above, which is not achievable with exclusively radiofrequency-powered devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating tissue, the method comprising:
   positioning a medical device proximate a first tissue area, the medical device including:
      an elongate catheter body having a proximal portion and a distal portion;
      an expandable first treatment region coupled to the distal portion of the elongate catheter body; and
      a second treatment region coupled to the distal portion of the catheter body at a location that is distal to the expandable first treatment region and defines an outer surface and a distal tip of the medical device;
   activating the expandable first treatment region to create a first treatment pattern in the first tissue area;
   deactivating the expandable first treatment region;
   repositioning the medical device such that the second treatment region is proximate a second tissue area; and
   activating the second treatment region to treat a second treatment pattern in the second tissue area, the second treatment pattern being different than the first treatment pattern.

2. The method of claim 1, wherein the second treatment region is at least one of a radiofrequency treatment region and an electroporation treatment region.

3. The method of claim 1, wherein the second treatment region includes at least one electrode.

4. The method of claim 3, wherein the second treatment region is an electroporation treatment region.

5. The method of claim 4, further comprising a power source in communication with the at least one electrode and being configured to transmit electrical pulses, activation of the second treatment region including delivering electrical pulses from the at least one electrode to the second tissue area.

6. The method of claim 3, wherein the second treatment region is an electroporation treatment region that includes a substantially linear segment.

7. The method of claim 3, wherein the second treatment region is a radiofrequency treatment region, activation of the second treatment region including:
   delivering radiofrequency energy to the at least one electrode;
   continuously monitoring a temperature of the at least one electrode; and
   modulating the radiofrequency energy delivered to the at least one electrode based on the temperature of the at least one electrode.

8. The method of claim 1, wherein the medical device further includes a deflectable segment located between the expandable first treatment region and the second treatment region.

9. The method of claim 8, wherein the deflectable segment has a flexibility that is greater than a flexibility of the second treatment region.

10. The method of claim 1, wherein the expandable first treatment region is a cryogenic treatment region.

11. The method of claim 10, wherein the cryogenic treatment region includes a balloon.

12. The method of claim 10, wherein the cryogenic treatment region includes a first expandable element and a second expandable element within the first expandable element.

13. The method of claim 10, wherein activating the cryogenic treatment region includes circulating coolant within the cryogenic treatment region.

14. A method of ablating tissue, the method comprising:
   navigating a medical device to a location within a patient's body, the medical device including:
      an elongate catheter body having a proximal portion and a distal portion;
      a first treatment region coupled to the distal portion of the catheter body; and
      a second treatment region coupled to the distal portion of the catheter body at a location that is distal to the first treatment region and defines an outer surface and a distal tip of the medical device, the first and second treatment regions being independently operable;
   activating the first treatment region to create a first treatment pattern in a first tissue area;
   repositioning the medical device and deflecting the second treatment region such that the second treatment region is proximate a second tissue area, the second treatment region being deflectable independently of the first treatment region; and
   activating the second treatment region to treat a second treatment pattern in the second tissue area, the second treatment pattern being different than the first treatment pattern.

15. The method of claim 14, wherein the medical device further includes a deflectable segment located between the first treatment region and the second treatment region.

16. The method of claim 15, wherein the deflectable segment has a flexibility that is greater than a flexibility of the second treatment region.

17. The method of claim 14, wherein the first treatment region is an expandable cryogenic treatment region.

18. The method of claim 17, wherein the second treatment region is at least one of a radiofrequency treatment region and an electroporation treatment region.

19. The method of claim 14, wherein the medical device further includes a sensor coupled to at least one of the first treatment region and the second treatment region, the method further comprising continuously monitoring a temperature of the first and second treatment regions.

* * * * *